(12) United States Patent
Provost et al.

(10) Patent No.: US 12,397,103 B2
(45) Date of Patent: Aug. 26, 2025

(54) INFUSION LINE SYSTEMS

(71) Applicant: Orion Innovations Inc., St. George, UT (US)

(72) Inventors: Wayne A. Provost, St. George, UT (US); Jeffrey D. Stewart, Washington, UT (US)

(73) Assignee: ORION INNOVATIONS INC., St. George, UT (US)

( * ) Notice: Subject to any disclaimer, the term of this patent is extended or adjusted under 35 U.S.C. 154(b) by 0 days.

(21) Appl. No.: 18/653,817

(22) Filed: May 2, 2024

(65) Prior Publication Data

US 2024/0350721 A1    Oct. 24, 2024

Related U.S. Application Data

(63) Continuation of application No. 18/120,935, filed on Mar. 13, 2023, now Pat. No. 11,992,648, which is a
(Continued)

(51) Int. Cl.
   *A61M 5/14*    (2006.01)
   *A61M 39/10*   (2006.01)
   (Continued)

(52) U.S. Cl.
   CPC .............. *A61M 5/14* (2013.01); *A61M 39/10* (2013.01); *G02B 6/0006* (2013.01); *G06F 21/35* (2013.01);
   (Continued)

(58) Field of Classification Search
   CPC .......... A61B 17/3403; A61B 5/150748; A61B 2017/00057; F21V 33/0068;
   (Continued)

(56) References Cited

U.S. PATENT DOCUMENTS 5,316,473 A    5/1994   Hare
6,984,052 B1 *  1/2006  Del Castillo ........ A61M 5/1411
                                                  362/253
(Continued)

FOREIGN PATENT DOCUMENTS

CN    104548260 A    4/2015
EP    2371411 A1    10/2011
(Continued)

OTHER PUBLICATIONS

International Search Report and Written Opinion received for PCT Patent Application No. PCT/US2023/077229, mailed on Feb. 22, 2024, 12 pages.
(Continued)

*Primary Examiner* — William J Carter
(74) *Attorney, Agent, or Firm* — Workman Nydegger

(57) ABSTRACT

An IV-line identification system to enable ready identification of an IV line and its associated fluid source and output from other IV lines with their fluid sources and outputs. The IV-line identification system includes an optical member affixed along a longitudinal length of an elongated member that transmits light when a light source provides a light to the optical member.

19 Claims, 14 Drawing Sheets

Related U.S. Application Data continuation of application No. 17/564,587, filed on Dec. 29, 2021, now Pat. No. 11,623,035, which is a continuation of application No. 17/191,674, filed on Mar. 3, 2021, now Pat. No. 11,241,528, which is a continuation of application No. 16/909,111, filed on Jun. 23, 2020, now Pat. No. 10,967,116, which is a continuation of application No. 16/548,067, filed on Aug. 22, 2019, now Pat. No. 10,722,641, which is a continuation of application No. 16/053,495, filed on Aug. 2, 2018, now Pat. No. 10,589,019, which is a continuation of application No. 15/902,682, filed on Feb. 22, 2018, now Pat. No. 10,064,991, which is a continuation-in-part of application No. 15/618,799, filed on Jun. 9, 2017, now abandoned.

(60) Provisional application No. 62/354,617, filed on Jun. 24, 2016.

(51) Int. Cl.
    *F21V 8/00*     (2006.01)
    *G06F 21/35*     (2013.01)

(52) U.S. Cl.
    CPC ............... *A61M 2205/587* (2013.01); *A61M 2205/6081* (2013.01); *G02B 6/001* (2013.01)

(58) Field of Classification Search
    CPC ...... F21V 33/0072; F21V 21/088; F21V 8/00; A61M 5/14; A61M 39/10; F06F 21/35
    See application file for complete search history.

(56) References Cited

U.S. PATENT DOCUMENTS

| | | |
|---|---|---|
| D518,261 S | 3/2006 | Varga |
| 9,308,051 B2 | 4/2016 | Adams et al. |
| 10,639,416 B2 | 5/2020 | Utz |
| 10,722,641 B2 | 7/2020 | Provost et al. |
| 11,241,528 B2 | 2/2022 | Provost et al. |
| 2004/0160770 A1* | 8/2004 | Rodriguez .......... A61M 5/1417 362/234 |
| 2007/0088286 A1 | 4/2007 | Brier |
| 2007/0100222 A1 | 5/2007 | Mastrototaro et al. |
| 2007/0106263 A1 | 5/2007 | Ward |
| 2008/0033519 A1* | 2/2008 | Burwell ............... A61N 5/0601 607/122 |
| 2008/0177145 A1 | 7/2008 | Furnish |
| 2011/0197397 A1 | 8/2011 | Pang |
| 2013/0208497 A1* | 8/2013 | Provost ............... F21V 33/0068 362/555 |
| 2014/0061421 A1 | 3/2014 | Lane |
| 2014/0327759 A1 | 11/2014 | Tao |
| 2017/0216522 A1 | 8/2017 | Slepicka et al. |
| 2017/0258983 A1 | 9/2017 | Utz |
| 2017/0368255 A1 | 12/2017 | Provost et al. |
| 2018/0140770 A1 | 5/2018 | Hetchler et al. |
| 2018/0177938 A1 | 6/2018 | Provost et al. |
| 2018/0344923 A1 | 12/2018 | Provost et al. |
| 2019/0374703 A1 | 12/2019 | Provost et al. |
| 2020/0316288 A1 | 10/2020 | Provost et al. |
| 2021/0187187 A1 | 6/2021 | Provost et al. |
| 2022/0118174 A1 | 4/2022 | Provost et al. |
| 2022/0143313 A1 | 5/2022 | Lee et al. |
| 2023/0293807 A1 | 9/2023 | Provost et al. |
| 2024/0123136 A1 | 4/2024 | Provost |
| 2024/0123209 A1 | 4/2024 | Provost et al. |

FOREIGN PATENT DOCUMENTS

| | | |
|---|---|---|
| WO | 2010/010358 A1 | 1/2010 |
| WO | 2011/127043 A1 | 10/2011 |
| WO | 2013/192235 A1 | 12/2013 |
| WO | 2022/212560 A1 | 10/2022 |

OTHER PUBLICATIONS

International Search Report and Written Opinion received for PCT Patent Application No. PCT/US2023/077231, mailed on Feb. 23, 2024, 27 pages.
Final Office Action received for U.S. Appl. No. 15/618,799, mailed on Jul. 14, 2020, 17 pages.
International Search Report and Written Opinion for PCT/US02019/018826 dated May 22, 2019.
Non-Final Office Action received for U.S. Appl. No. 16/909,111, mailed on Jul. 20, 2020, 9 pages.
Non-Final Office Action received for U.S. Appl. No. 17/564,587, mailed on Jul. 18, 2022, 9 pages.
Notice of Allowance received for U.S. Appl. No. 16/909,111, mailed on Dec. 3, 2020, 10 pages.
Office Action received for U.S. Appl. No. 15/618,799, mailed on Oct. 28, 2019.
Office Action received for U.S. Appl. No. 16/053,495, mailed on Sep. 24, 2018.
Office Action received for U.S. Appl. No. 16/548,067, mailed on Sep. 12, 2019.

* cited by examiner

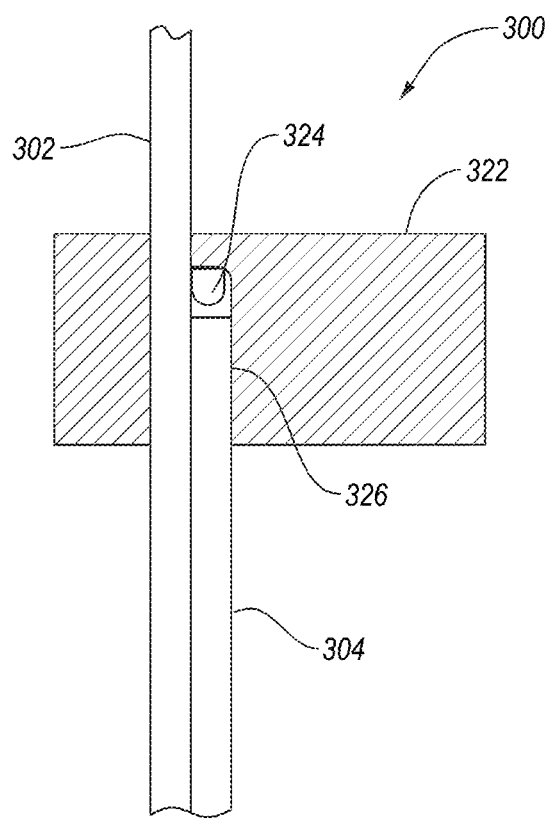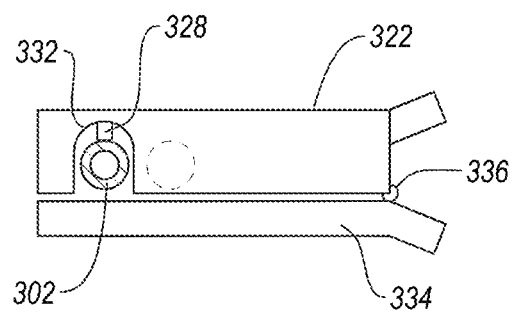
FIG. 9AFIG. 9B

INFUSION LINE SYSTEMS

CROSS-REFERENCE TO RELATED APPLICATIONS

This application is a continuation of U.S. application Ser. No. 18/120,935, filed Mar. 13, 2023, titled "INFUSION LINE SYSTEMS," which is a continuation of U.S. application Ser. No. 17/564,587, filed Dec. 29, 2021, now U.S. Pat. No. 11,623,035, issued on Nov. 4, 2023, titled "INFUSION LINE SYSTEMS," which is a continuation of U.S. application Ser. No. 17/191,674, filed Mar. 3, 2021, now U.S. Pat. No. 11,241,528, issued on Aug. 2, 2022, titled "INFUSION LINE SYSTEMS," which is a continuation of U.S. application Ser. No. 16/909,111, filed Jun. 23, 2020, now U.S. Pat. No. 10,967,116, issued Jun. 4, 2021, titled "INFUSION LINE SYSTEMS," which is a continuation of U.S. application Ser. No. 16/548,067, filed Aug. 22, 2019, now U.S. Pat. No. 10,722,641, issued on Jul. 28, 2020, titled "INFUSION LINE SYSTEMS," which is a continuation of U.S. application Ser. No. 16/053,495, filed Aug. 2, 2018, now U.S. Pat. No. 10,589,019, issued on Mar. 17, 2020, titled "INFUSION LINE SYSTEMS," which is a continuation of U.S. application Ser. No. 15/902,682, filed Feb. 22, 2018, now U.S. Pat. No. 10,064,991, issued on Apr. 9, 2018, titled "INFUSION LINE SYSTEMS," which is a continuation-in-part of U.S. application Ser. No. 15/618,799, filed Jun. 9, 2017, titled "ILLUMINATED INFUSION LINE AND SYSTEMS," which claims priority to and the benefit of U.S. Provisional Patent Application Ser. No. 62/354,617, filed Jun. 24, 2016, titled "ILLUMINATED INFUSION LINE AND SYSTEMS," each of the foregoing of which are incorporated herein in their entireties.

BACKGROUND

1. The Field of the Invention

The present disclosure generally relates to systems for the intravenous administration of medications, fluids, and/or nutrients. More particularly, the disclosure relates to systems and devices for distinctly identifying each of several intravenous lines used to intravenously administer medications, fluids, and/or nutrients.

2. The Relevant Technology

In a hospital setting, patients are often administered liquid medications, fluids, and nutrients (hereinafter collectively referred to as "therapeutic fluids") via intravenous lines (hereinafter referred to as "IV lines"). IV lines generally consist of flexible, plastic tubing connected at one end to a fluid source and at another end to a needle or port that provides access to a blood vessel/artery of a patient. It is not uncommon for multiple IV lines, each connected to a different source of fluid, to be used simultaneously to deliver several therapeutic fluids at once to a single patient. It is also not uncommon for the needles or ports to be located adjacent to one another, such as multiple adjacent needles providing access into the brachial vein running through the arm of the patient.

While the simultaneous use of multiple IV lines can provide numerous benefits, some challenges can also be encountered. For instance, when multiple IV lines are used to administer multiple therapeutic fluids to a single patient, it can become cumbersome and difficult to readily identify one IV line from another. Thus, it can be difficult to quickly and accurately identify a particular therapeutic fluid source and corresponding therapeutic fluid output compared to another medication source and its corresponding therapeutic fluid output. This problem is aggravated by the tendency of each of the intravenous lines to coil up to their packaged configuration and consequently tangle with other IV lines or tangle under bed sheets or clothing.

Quick identification of a particular therapeutic fluid source is often required in emergency situations. For example, when a patient hooked up to multiple IV lines is in need of emergency intravenous administration of a therapeutic fluid not currently being provided through one of the IV lines, it is necessary to immediately provide that therapeutic fluid. If a blood vessel cannot rapidly be located into which the therapeutic fluid can be injected, it is common practice to provide the drug through an IV line in which a therapeutic fluid is already being administered. This practice of using existing IV lines to administer new therapeutic fluids is also common in non-emergency situations. The person administering the drug, however, must be sure that the IV line through which the new therapeutic fluid is administered is carrying a therapeutic fluid which is compatible with the new therapeutic fluid. Severe results may occur if a new therapeutic fluid is injected through an IV line in which the therapeutic fluid already flowing therethrough is not compatible with the new therapeutic fluid. For example, if heparin is injected into an IV line through which lidocaine is already flowing, a flakey precipitate will form in the mixture which can be dangerous to a patient. Similarly, mixing insulin with certain chemotherapy drugs in a common IV line can be extremely dangerous for a patient.

As a result of the difficulties in distinguishing between multiple IV lines and their associated fluid sources and outputs and the potentially life-threatening possibilities that can occur if incompatible therapeutic fluids are injected through the same IV line, there is a need for devices and systems that allow for ready and accurate identification of individual IV lines with their associated fluid sources and outputs.

BRIEF SUMMARY

In an embodiment, an intravenous infusion line assembly includes an elongated member and an optical member. The elongated member has a fluid conduit for administering therapeutic fluid to a patient by providing fluid communication between a first end of the elongated member and a second end of the elongated member. The optical member is affixed along a longitudinal length of the elongated member between the first end and the second end of the elongated member. The optical member is also at least partially optically transmissive to internally reflect light within the optical member.

In another embodiment, an intravenous infusion line identification system includes an intravenous therapy system for administering therapeutic fluid to a patient and a light source. The intravenous therapy system includes a therapeutic fluid input and a therapeutic fluid output with an elongated member and optical member. The elongated member provides fluid communication from the therapeutic fluid input to the therapeutic fluid output. The optical member is affixed along a longitudinal length of the elongated member. The optical member is also at least partially optically transmissive to internally reflect light within the optical member. In some configurations, the optical member is affixed along the longitudinal length of the elongated member by a direct bond, an adhesive, or a partial melting between the optical member and the elongated member. The light source is selectively couplable to the optical member and configured to provide light to the optical member.

In yet another embodiment, a method for implementing an IV-line identification system includes an act of providing an infusion line that includes an optical member affixed along a longitudinal length of the infusion line, selectively coupling a light source to the optical member, and directing a light from the light source into the optical member. In some implementations, the optical member is at least partially optically transmissive to internally reflect light within the optical member.

These and other objects and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only illustrated embodiments of the invention and are therefore not to be considered limiting of its scope. The invention will be described and explained with additional specificity and detail through the use of the accompanying drawings in which:

FIG. 9A is a partial cutaway side view of the embodiment of an IV infusion line identification system of FIG. 8, according to the present disclosure;

FIG. 9B is a partial cutaway end view of the embodiment of an IV infusion line identification system of FIG. 8, according to the present disclosure;

DETAILED DESCRIPTION

Figure 1:
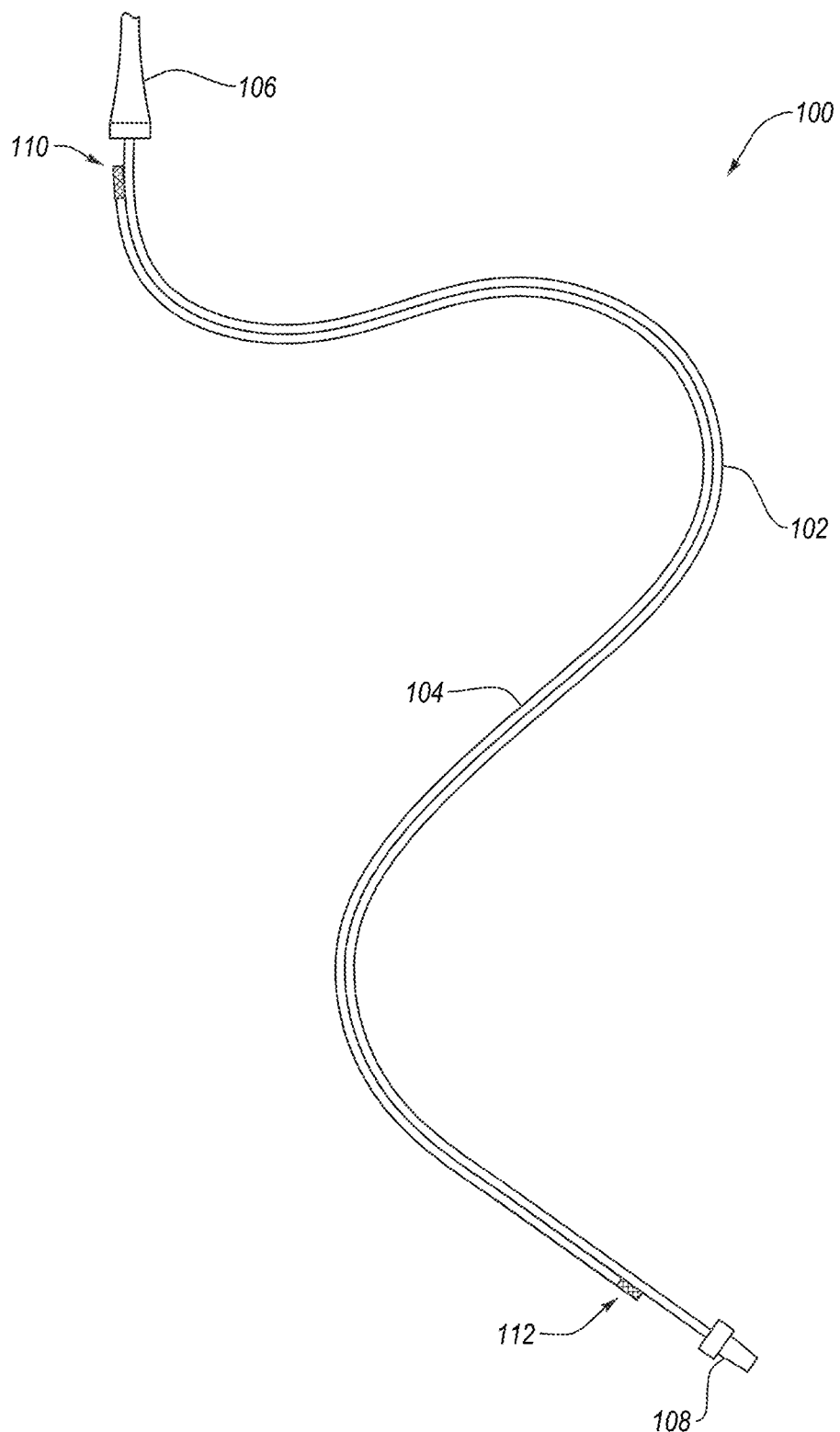
FIG. 1 illustrates a schematic view of an embodiment of an intravenous ("IV") infusion line assembly, according to the present disclosure, where a first light component is a light source and where a second light component is an optical member operatively coupled to the light source such that both the first and second light components provide synchronous visual identifiers.

The embodiments described herein extend to methods, devices, systems, assemblies, and apparatus for identification of intravenous ("IV") infusion lines. Such are configured to, for example, enable the reliable identification of one IV infusion line from another in a simple and efficient manner to prevent the inadvertent injection of incompatible therapeutic fluids through a single IV infusion line. An IV infusion line identification system, as described herein, may reduce the number of misidentified infusion lines without significant changes to the existing clinical methods and/or equipment.

Reference will now be made to the drawings to describe various aspects of exemplary embodiments of the invention. It is understood that the drawings are diagrammatic and schematic representations of such exemplary embodiments, and are not limiting of the present invention, nor are any particular elements to be considered essential for all embodiments or that elements be assembled or manufactured in any particular order or manner. No inference should therefore be drawn from the drawings as to the necessity of any element. In the following description, numerous specific details are set forth in order to provide a thorough understanding of the present invention. It will be obvious, however, to one of ordinary skill in the art that the present invention may be practiced without these specific details. In other cases, well known aspects of IV lines and related devices and methods, general manufacturing techniques, and the like are not described in detail herein in order to avoid unnecessarily obscuring the novel aspects of the present invention.

FIGS. 1 through 12 and the following discussion are intended to provide a brief general description of exemplary devices in which embodiments of the invention may be implemented. While IV therapy apparatuses for administering therapeutic fluids are described below, this is but one single exemplary application for the present invention, and embodiments of the invention may be implemented in other applications, both within the medical field and in other technical fields. Accordingly, throughout the specification and claims, references to medical devices and systems, such as "IV lines," "IV bags," "pumps," "needles," "ports," "IV therapy systems," and the like, are intended to apply broadly to any type of items that may need to be individually identified and distinguished from other similar items, as described herein.

Furthermore, while embodiments of IV therapy systems are shown and described, it will be understood that these are merely exemplary embodiments. Various components of these exemplary embodiments may be excluded or replaced with other components known and used in the art. By way of non-limiting example, some of the exemplary embodiments include IV bags, pumps, and connectors. Each of these components could be eliminated or replaced with other components. For instance, various types of pumps, or no pump at all, can be used with the systems. Similarly, various types of fluid sources and connectors other than IV bags and Y-connectors could be employed.

With reference to FIG. 1, there is illustrated an IV infusion line assembly 100 for use in administering therapeutic fluid to a patient. The IV infusion line assembly 100 includes an elongated member 102 with a fluid conduit thereto. The fluid conduit may provide fluid communication for one or more therapeutic fluids, such as saline, medications, or nutrients. The IV infusion line assembly 100 includes an optical member 104 that is at least partially affixed to the elongated member 102. The optical member 104 is at least partially optically transmissive, such that light may pass through the optical member 104.

In some embodiments, the elongated member 102 may have a therapeutic fluid input 106 and a therapeutic fluid output 108. The therapeutic fluid input 106 may allow the elongated member to connect to a reservoir of therapeutic fluid, such as an IV bag, a glass bottle, a plastic bottle, a syringe, or other sterile reservoir. At an opposing end of the elongated member 102 is a therapeutic fluid output 108. The therapeutic fluid output is configured to connect the elongated member 102 to an access device (not shown), such as a needle or port, so that the elongated member 102 can provide fluid communication to a patient.

The optical member 104 has a first end 110 and a second end 112. In some embodiments, the first end 110 is located proximate the therapeutic fluid input 106 of the elongated member 102 and the second end 112 is located proximate the therapeutic fluid output 108 of the elongated member 102. At least a portion of the elongated member 102 and optical member 104 are fixed relative to one another. The elongated member 102 and optical member 104 are flexible, such that the optical member 104 and elongated member 102 may move as one or the other is moved. In some embodiments, the entire length of the optical member 104 is fixed to the elongated member 102. In other embodiments, a portion less than the entire length of the optical member 104 is fixed to the elongated member 102. In some embodiments, the first end 110 of the optical member 104 is fixed to the elongated member 102 and the second end 112 is fixed to the elongated member 102.

The optical member 104 may be optically transmissive to allow light to pass through and/or be transmitted by the optical member 104. In some embodiments, the optical member 104 may have a transmission percentage in visible wavelengths in a range having an upper value, a lower value, or upper and lower values including any of 40%, 45%, 50%, 55%, 60%, 65%, 70%, 75%, 80%, 85%, 90%, 95%, or any values therebetween. For example, the optical member 104 may have a transmission percentage in visible wavelengths greater than 40%. In other examples, the optical member 104 may have a transmission percentage in visible wavelength less than 95%. In yet other examples, the optical member 104 may have a transmission percentage between 40% and 95%. In further examples, the optical member 104 may have a transmission percentage between 50% and 90%.

In some embodiments, the optical member 104 may be a fiber optic cable. For example, at least a portion of a light that is provided at the first end 110 of the optical member 104 may be conveyed to the second end 112 of the optical member 104. The light may be conveyed from the first end 110 to the second end 112 via internal refraction. For example, the optical member 104 may have a first index of refraction and the surrounding environment, such as air, may have a second index of refraction that is less than the first index of refraction. The light may propagate along the inside of the optical member 104 in a longitudinal direction refracting off of the surface of the optical member 104 at an angle less than a critical angle, at least partially dependent on the relationship of the first index of refraction and the second index of refraction. In some embodiments, the optical member 104 may have an index of refraction greater than 1.5. In other embodiments, the optical member 104 may have an index of refraction greater than 1.8. In yet other embodiments, the optical member 104 may have an index of refraction greater than 2.0.

In some embodiments, the optical member 104 may be configured to convey at least a portion of the light in a longitudinal direction (i.e., from the first end 110 to the second end 112 or vice versa). The optical member 104 is configured to emit at least some of the light in a transverse direction (i.e. in a direction transverse to the longitudinal direction) and between the first end 110 and the second end 112. For example, when a light is provided at the first end 110 of the optical member 104, at least 10% of the light is emitted transversely along the length of the optical member 104. In other examples, when a light is provided at the first end 110 of the optical member 104, at least 20% of the light is emitted transversely along the length of the optical member 104. In yet other examples, when a light is provided at the first end 110 of the optical member 104, at least 30% of the light is emitted transversely along the length of the optical member 104. In at least one example, when a light is provided at the first end 110 of the optical member 104, at least 50% of the light is emitted transversely along the length of the optical member 104.

Figure 2:
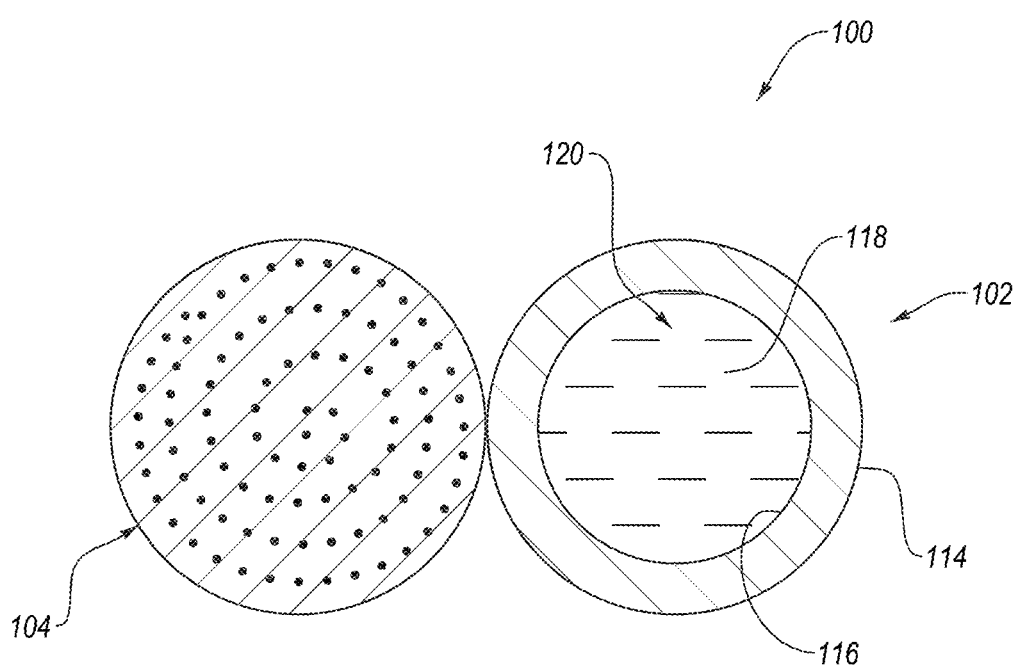
FIG. 2 illustrates a transverse cross-sectional view of the embodiment of an IV infusion line assembly of FIG. 1, according to the present disclosure.
Figure 3A:
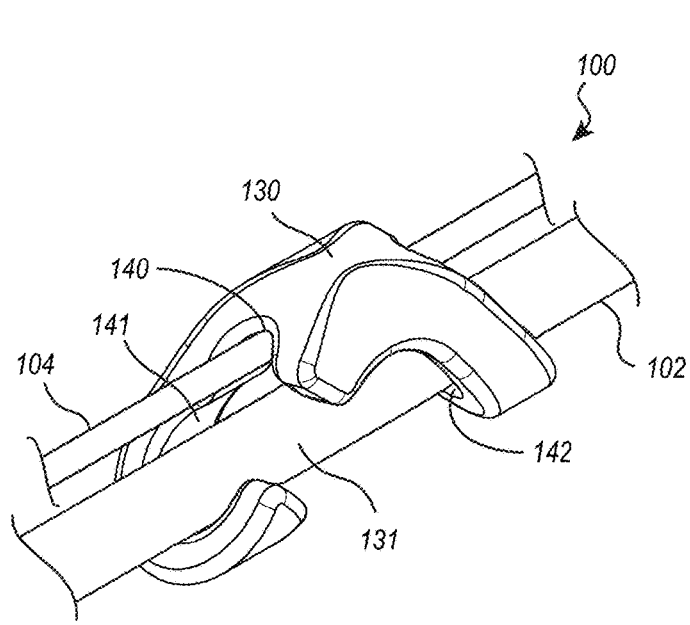
FIG. 3A illustrates a perspective view of an embodiment of the IV infusion line assembly, according to the present disclosure.
Figure 3B:
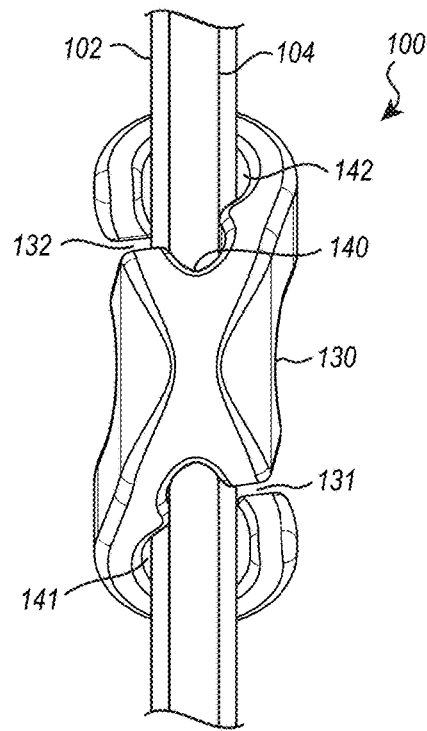
FIG. 3B illustrates a top view of an embodiment of the IV infusion line assembly, according to the present disclosure.
Figure 3C:
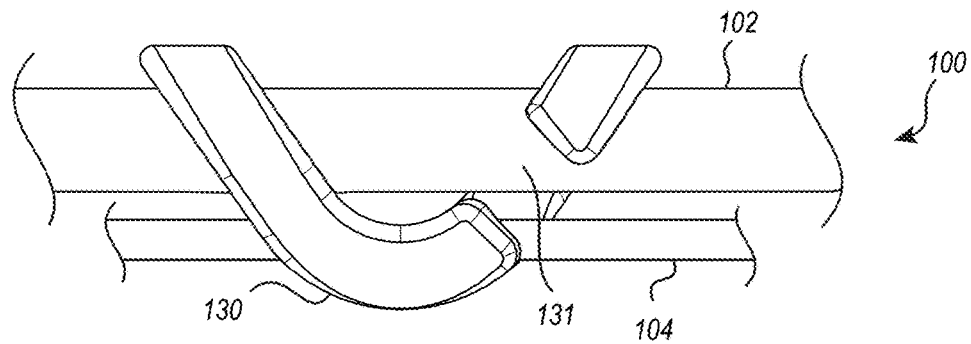
FIG. 3C illustrates a right side view of an embodiment of the IV infusion line assembly, according to the present disclosure.
Figure 3D:
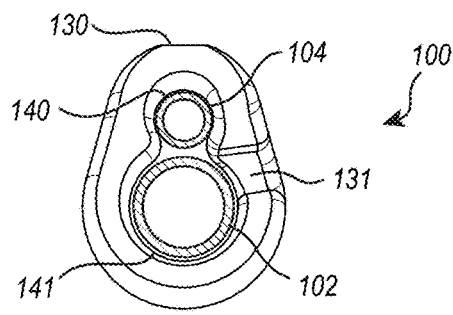
FIG. 3D illustrates a cross-sectional front view of an embodiment of the IV infusion line assembly, according to the present disclosure.
Figure 3E:
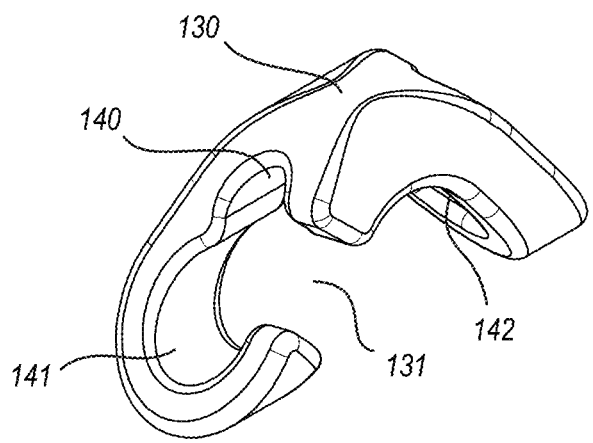
FIG. 3E illustrates a perspective view of a line fastener, according to the present disclosure.
Figure 3F:
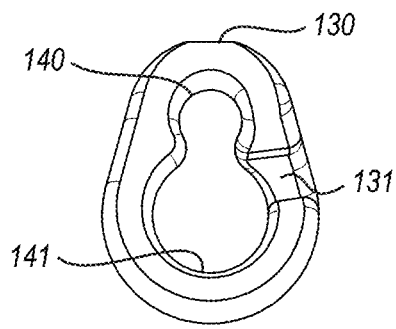
FIG. 3F illustrates a front view of a line fastener, according to the present disclosure.
Figure 3G:
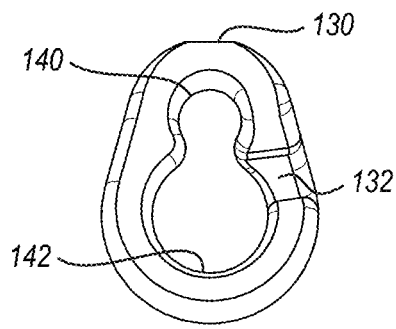
FIG. 3G illustrates a rear view of a line fastener, according to the present disclosure.
Figure 3H:
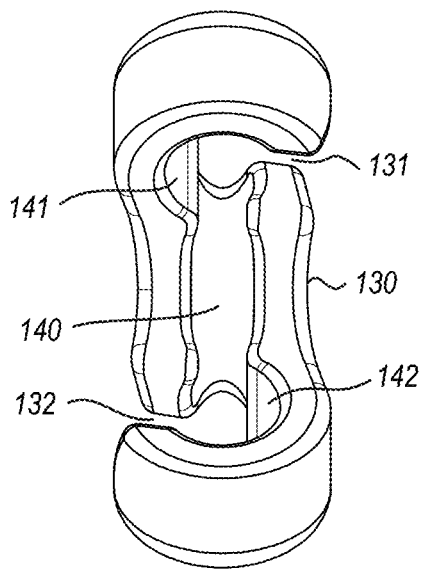
FIG. 3H illustrates a bottom view of a line fastener, according to the present disclosure.
Figure 3I:
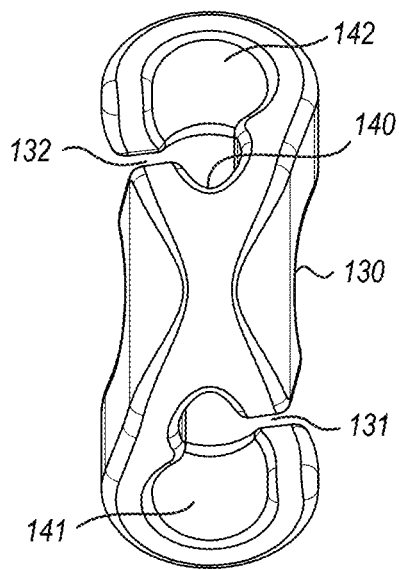
FIG. 3I illustrates a top view of a line fastener, according to the present disclosure.
Figure 3K:
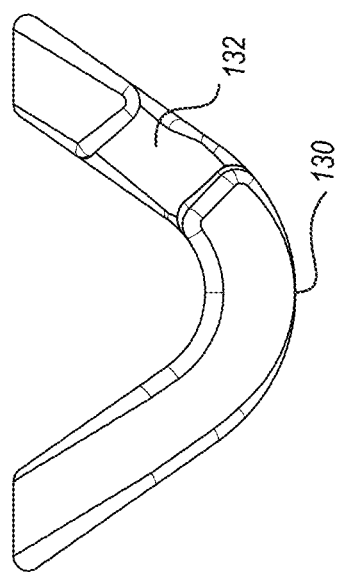
FIG. 3K illustrates a left side view of a line fastener, according to the present disclosure.
Figure 3J:
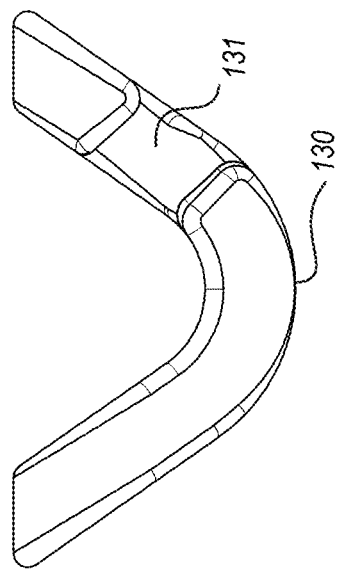
FIG. 3J illustrates a right side view of a line fastener, according to the present disclosure.

FIG. 2 illustrates a transverse cross-sectional view of the IV infusion line assembly 100 of FIG. 1. The elongated member 102 has an outer surface 114 and an inner surface 116. The inner surface 116 defines a fluid conduit 118 that extends longitudinally through the elongated member to provide fluid communication therethrough. The fluid 120 may be a therapeutic fluid provided from a reservoir to a patient.

In some embodiments, the optical member 104 may be uniform along a length thereof. In other embodiments the optical member 104, as shown in FIG. 2, includes a plurality of scattering elements embedded in the optical member 104 to scatter light transmitted therethrough and emit the light through a sidewall of the optical member 104.

In some embodiments, the optical member 104 may be at least partially affixed to the outer surface 114 of the elongated member 102. For example, the optical member 104 may be affixed to the outer surface 114 of the elongated member 102 with a plurality of fasteners or clamps. In other examples, the optical member 104 may be adhered to the outer surface 114 with an adhesive positioned therebetween. In yet other examples, the optical member 104 may be directly bonded to the elongated member 102, such as by partially melting of the optical member 104 and/or elongated member 102 to bond the material of the optical member 104 and elongated member 102. The optical member 104 and elongated member 102 may be bonded together by sonic welding, by frictional welding, by application of heat from an external source, or by other partial melting methods. Embodiments may include any combination of said or other means for at least partially affixing the optical member 104 to the outer surface 114 of the elongated member 102.

FIGS. 3A through 3D illustrate various views of an embodiment of the IV infusion line assembly 100 of FIG. 1 in which the optical member 104 is at least partially coupled to the elongated member 102 with a plurality of line fasteners 130 (also referred to herein as "rigid clamps"). As used herein, the "rigid clamps" are "rigid" in that they do not necessarily require moving parts for adapting to and fastening the optical member 104 and elongated member 102. The "rigid clamps" may therefore include an amount of flexibility inherent in the material in which they are made (e.g., a suitable polymer or metal material).

The rigid clamps 130 include a first opening 131 and a second opening 132, each adapted to receiving the optical member 104 and the elongated member 102. The rigid clamps 130 have a first groove 140 adapted to removably secure the optical member 104. The rigid clamps 130 also have a second groove 141 and a third groove 142, which are adapted to, in tandem, removably secure the elongated member 102. For example, a user may loop the optical member 104 and elongated member 102 through the respective openings 131 and 132, may position the optical member 104 within the first groove 140, and may position the elongated member 102 within the second groove 141 and third groove 142.

In one of arrangement, the rigid clamps 130 are spaced about six to eight inches apart along the length of the IV infusion line assembly 100. Although six to eight inch spacing is the presently preferred configuration, other configurations may include tighter spacing (e.g., a half inch of space between the rigid clamps 130 along the length of the IV infusion line assembly 100), looser spacing (e.g., fourteen inches of space between the rigid clamps 130 along the length of the IV infusion line assembly 100), a non-uniform spacing arrangement (e.g., with variable spacing between the rigid clamps 130 along the length of the IV infusion line assembly 100), etcetera.

FIGS. 3E through 3K show additional views of the exemplary rigid clamp 130. In the illustrated embodiment, the first groove 140 has a smaller diameter than that of the second and third grooves 141 and 142. Such a configuration beneficially allows the relatively smaller optical member 104 to engage with the first groove 140 while the relatively larger elongated member 102 engages with the second and third grooves 141 and 142. In other embodiments, the groove sizes may be adjusted according to corresponding sizes of elongated members and/or optical members. In some implementations, the positions of the elongated member 102 and the optical member 104 may be reversed. Other embodiments may additionally or alternatively use other types of fasteners or clamps (e.g., spring-loaded clamps, hinged clasps) to at least partially couple the optical member 104 to the elongated member 102.

In some embodiments, the connection between the elongated member 102 and the optical member 104 may be breakable by a user. For example, at least a portion of the longitudinal length of the connection between the elongated member 102 and optical member 104 may be broken (e.g., the elongated member 102 and optical member 104 may be pulled apart from one another) to allow the use of inline filters, rotary pumps, or for connection of other devices, as needed by a user.

Figure 4:
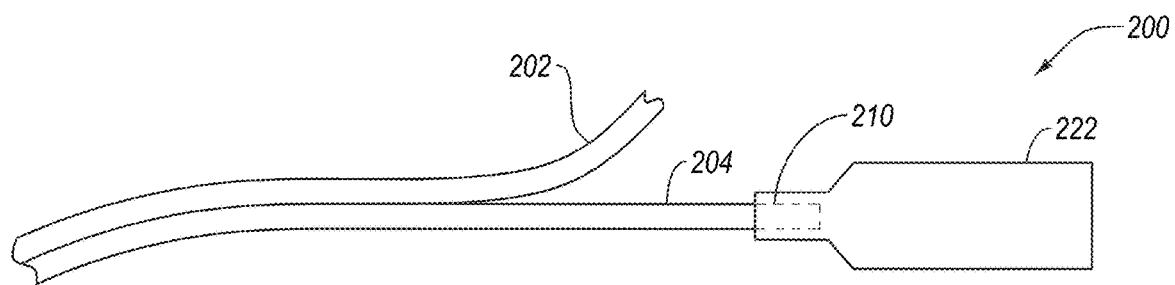
FIG. 4 is a side view of an embodiment of an IV infusion line identification system, according to the present disclosure.

For example, FIG. 4 illustrates an embodiment of an IV infusion line identification system with an IV infusion line assembly 200 with at least a portion of the optical member 204 branched from the elongated member 202 to allow a light source 222 to connect to the optical member 204. The light source 222 may be coupled to the IV infusion line assembly 200 prior to a sterilization procedure (e.g., gamma radiation, ethylene oxide gas). Alternatively, the light source 222 may be a portable light source reusable with a plurality of IV infusion line assemblies 200. For example, a user, such as a doctor, a nurse practitioner, a physician's assistant, etc., may carry a light source 222 as described herein, and use the light source with a plurality of IV infusion line assemblies 200 on a single patient or with multiple patients. Typically, however, the light source 222 will be coupled to the IV infusion line assembly 200 prior to sterilization so that the system may be provided to users in a sterile and ready-to-use state.

The light source 222 may be selectively coupled to the optical member 204 to provide a light to the optical member 204. The light source 222 may include an outboard power supply, such as a rechargeable and/or replaceable battery, allowing the light source 222 to be carried with a user. In other embodiments, the light source 222 may have one or more connectors to allow the light source 222 to be connected to an external power source. The light source 222 may provide light to the first end 210 of the optical member 204 to illuminate the optical member 204 along a longitudinal length of the optical member 204. In other embodiments, the light source 222 may provide light to the second end (e.g., the second end 112 as shown in FIG. 1) of the optical member 204 and illuminate the optical member 204 along a longitudinal length of the optical member 204.

Figure 5:
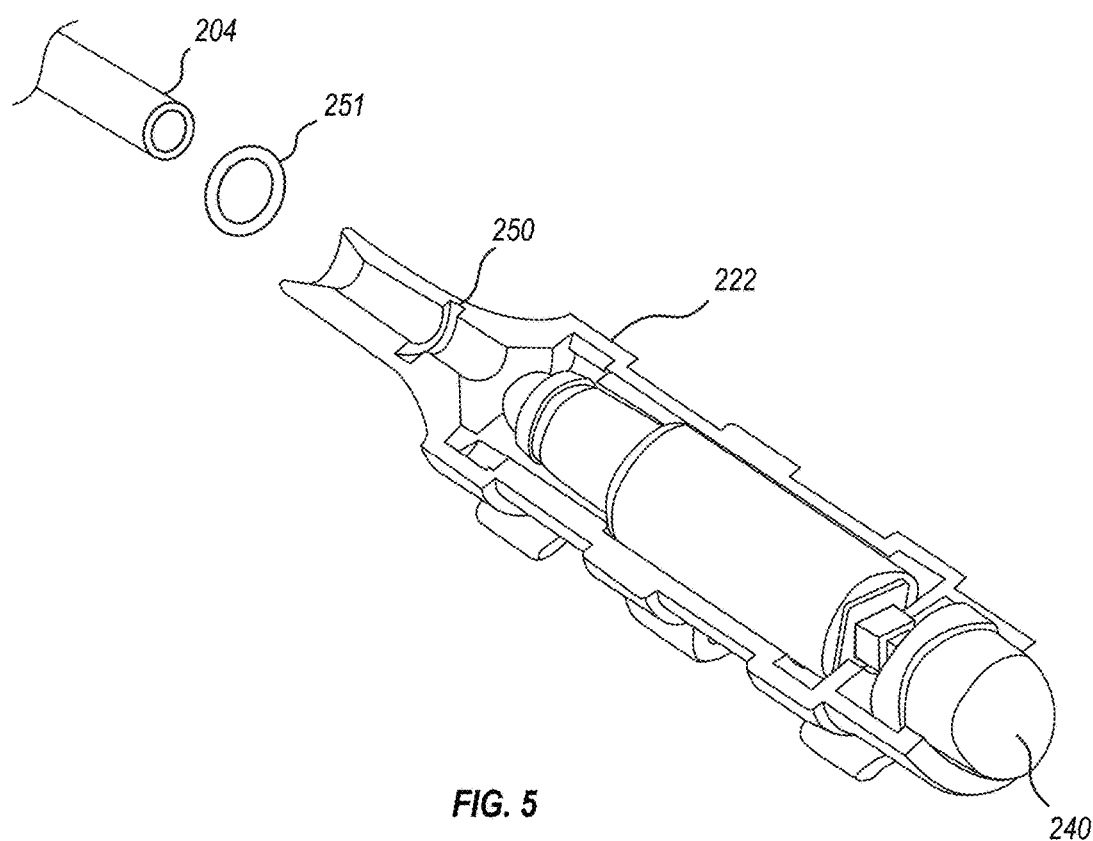
FIG. 5 illustrates an exploded perspective view of an embodiment of a light source, according to the present disclosure.

FIG. 5 illustrates an exploded view of an embodiment of a light source 222 of FIG. 4. The light source 222 includes an O-ring slot 250 for receiving an O-ring 251. The O-ring 251 is adapted to removably secure the optical member 204 to provide selective coupling between the optical member 204 and the light source 222. Other embodiments may additionally or alternatively use other means for effecting selective coupling between the optical member 204 and the light source 222 (e.g., friction fitting, adhesive, clamps).

Figure 6:
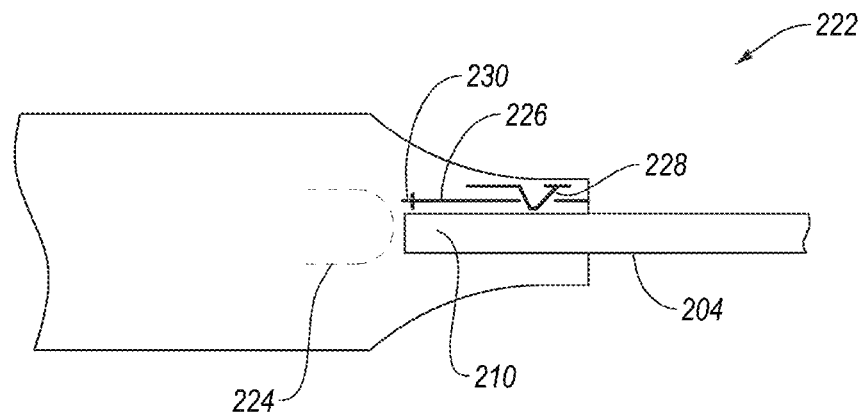
FIG. 6 is a partial cutaway side view of the embodiment of an IV infusion line identification system of FIG. 4, according to the present disclosure.

In some embodiments, the light source 222 may be activated by a user-operated manual switch, such as the illustrated push button 240. Although the user operable manual switch is a presently preferred embodiment, other embodiments may include systems for automatically activating the light source 222 upon coupling the optical member 204 to the light source 222, as described below with respect to FIG. 6. FIG. 6 illustrates a cross-sectional view of one optional configuration of the light source 222 of FIG. 4 which includes a sensor for automatic actuation of the light source 222 (e.g., as an alternative to a manual switch). The light source 222 may have a light emitting diode ("LED") 224, light bulb, laser diode, or other photon source positioned adjacent a cavity 226 in the light source 222. The cavity 226 may have a sensor 228 positioned in a side of the cavity 226. The sensor 228 may be configured to sense the presence of an optical member 204 positioned in the cavity 226. The sensor 228 is operably coupled to the LED 224 to allow electricity to the LED 224 upon sensing the presence of the first end 210 (or second end) of the optical member 204 in the cavity 226. In other words, the light source 222 provides a light to the optical member 204 when the user inserts a portion of the optical member 204 into the light source 222. In some embodiments, the LED 224 may be positioned at a rear end 230 of the cavity 226. In other embodiments, the LED 224 may be positioned at other orientations to the cavity 226.

The sensor 228 may be a physical sensor, such as a switch, toggle, or button that senses the optical member 204 via mechanical contact with the optical member 204. In other embodiments, the sensor 228 may be an optical sensor, such an infrared sensor, UV sensor, laser sensor, or other sensor that senses the optical member 204 via interference between the optical member 204 and an emitted signal.

Figure 7A:
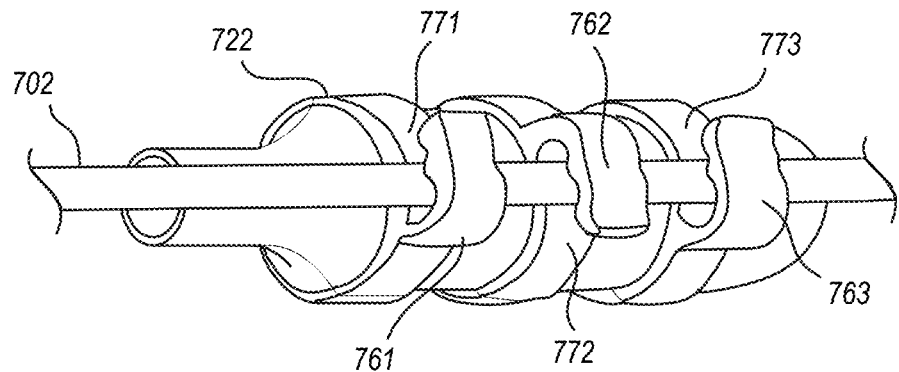
FIG. 7A illustrates an embodiment of a light source, according to the present disclosure.
Figure 7B:
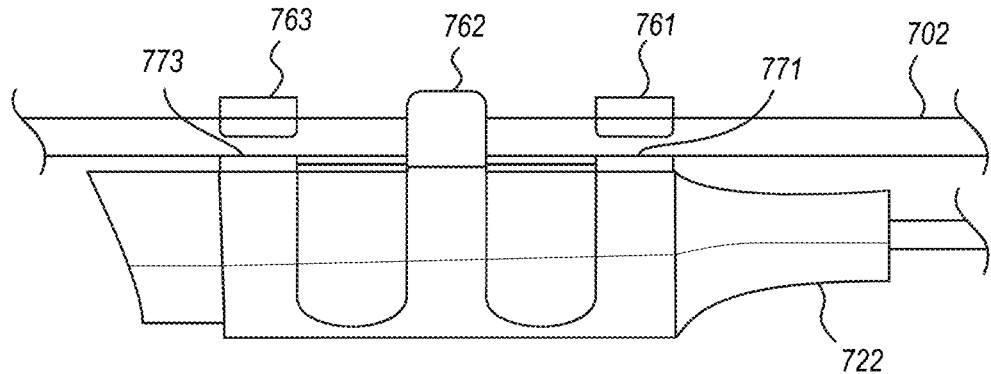
FIG. 7B illustrates a side view of the embodiment of a light source of FIG. 7A, according to the present disclosure.

FIGS. 7A and 7B illustrate another embodiment of a light source 722. The light source 722 may be configured in a fashion similar to that of the light source 222 of FIG. 4 except as noted below. The light source 722 may be selectively attachable to the elongated member 702 by means of a first clip 761 with a first opening 771 facing a first direction, a second clip 762 with a second opening 772 facing a second direction opposite the first direction, and a third clip 763 with a third opening 773 facing the first direction. Other embodiments may use a single clip. In such embodiments, the single clip may extend across approximately a majority of the length of the light source 722. Other embodiments may include a plurality of clips (with at least one facing an opposite direction from one other), a plurality of clips with openings facing the same direction, a channel groove, a plurality of channel grooves, or other structural configurations for making the light source 722 selectively attachable to the elongated member 702.

In the illustrated embodiment, the clips 761, 762, and 763 are arranged so as to be spread across a sufficient length of the light source 722 to provide a connection when the light source 722 is coupled to the elongated member 702. For example, the distance between the first clip 761 and third clip 763 may be about 50% to about 80% of the overall length of the light source 722.

As with other embodiments described herein, the light source, as a first light component, may be positioned near a first end the elongated member 702 (e.g., near the fluid input) and an optical member (not shown in this view), as a second light component, may extend and be positioned near a second end of the elongated member 702 (e.g., near the fluid output). The first and second light components are operatively coupled to one another such that when the first light component is activated to generate a light signal at the first end of the elongated member 702, a corresponding light signal will be generated at the second end of the elongated member 702 by way of the second light component.

Figure 8:
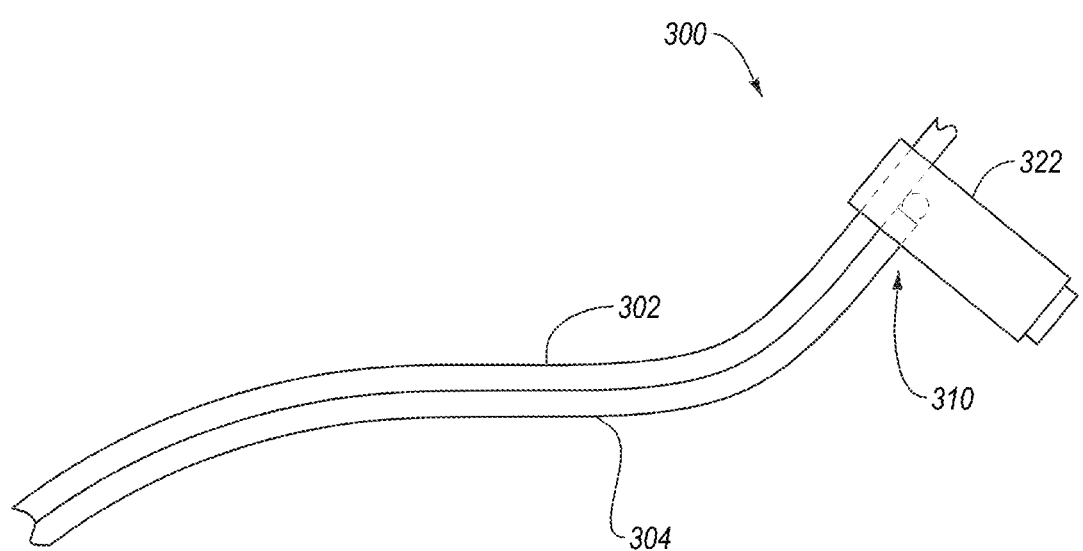
FIG. 8 is a side view of another embodiment of an IV infusion line identification system, according to the present disclosure.

FIG. 8 illustrates another embodiment of an IV infusion line identification system with an IV infusion line assembly 300 with a first end 310 of the optical member 304 coupled to the elongated member 302. The light source 322 is configured to connect over the elongated member 302 and the optical member 304 from the transverse direction to provide light to the first end 310 (or second end) of the optical member 304 without having to decouple an end of the optical member 304 and the elongated member 302.

FIGS. 9A and 9B show detail views of the embodiment of a light source 322 of FIG. 8. FIG. 9A shows a cross-sectional side view of the IV infusion line assembly 300 positioned in the light source 322. The cavity 326 of the light source 322 shown in FIGS. 9A and 9B is configured to allow the elongated member 302 to extend through the light source 322 while the optical member 304 terminated in the light source 322 adjacent an LED 324 (or other photon source).

FIG. 9B shows an end view of the light source 322 showing a sensor 328 in a wall 332 of the cavity 326 shown in FIG. 9A. Referring again to FIG. 9B, the sensor 328 may be configured to sense the presence of the elongated member 302 positioned in the light source 322. Similar to the sensor 228 described in relation to FIG. 6, the sensor 328 may be a physical sensor, such as a switch, toggle, or button that senses the elongated member 302 via mechanical contact with the elongated member 302. In other embodiments, the sensor 328 may be an optical sensor, such an infrared sensor, UV sensor, laser sensor, or other sensor that senses the elongated member 302 via interference between the elongated member 302 and an emitted signal.

In the depicted embodiment, the sensor 328 is depressed by the elongated member 302 when a force is applied to the elongated member 302 by a clip 334 of the light source 322. The clip 334 may be movably connected to the light source 322 about a hinged connection 336. The hinged connection 336 may be biased to close the clip 334 and/or hold the clip 334 closed against the light source 322. The bias of the hinged connection 336 may apply a sufficient force through the clip 334 to compress the elongated member 302 against the sensor 328. The bias of the hinged connection 336 may apply a sufficient force through the clip 334 to retain the light source 322 on the elongated member 302 when a user releases the light source 322. In other words, the user may clip the light source 322 onto the elongated member 302 and the light source 322 may hang in place on the elongate member 302 without the user continuing to support the light source 322.

Figure 10A:
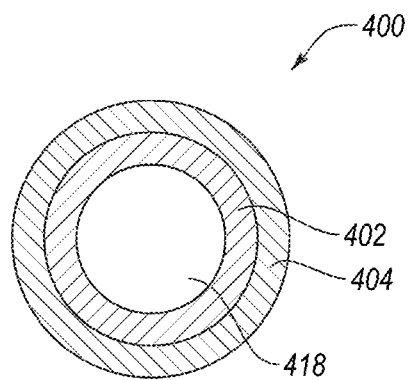
FIG. 10A is a transverse cross-sectional view of another embodiment of an IV infusion line, according to the present disclosure.

FIG. 10A illustrates a transverse cross-section of another embodiment of an IV infusion line assembly 400. The elongated member 402 defines a conduit 418 through the center of the elongated member 402 and an optical member 404 is positioned in contact with an outer surface of the elongated member 402. In some embodiments, the optical member 404 may be fixed to the outer surface of the elongated member 402. In other embodiments, the optical member 404 may be slidable in a longitudinal direction relative to the elongated member 402. In other word, the optical member 404 may be positioned circumferentially about the elongated member 402 but not fixed thereto.

Figure 10B:
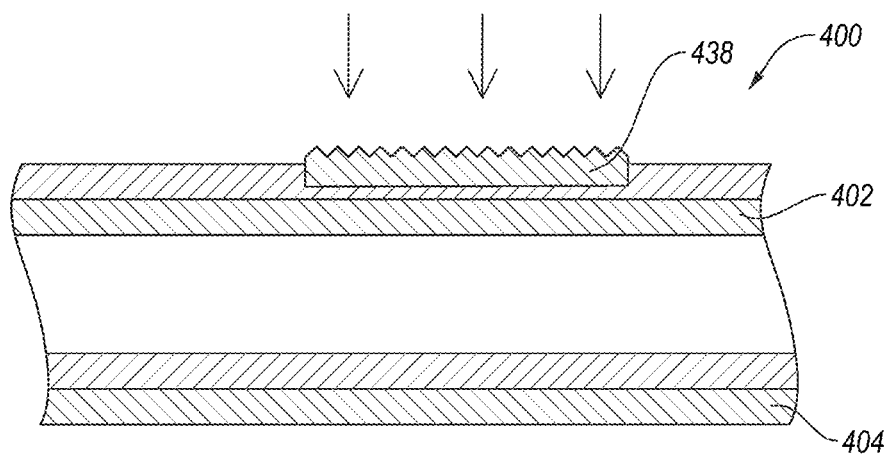
FIG. 10B is a longitudinal cross-sectional view of the embodiment of an IV infusion line of FIG. 10A, according to the present disclosure.

FIG. 10B illustrates a longitudinal cross-section of the embodiment of an IV infusion line assembly 400. In such embodiments, the optical member 404 may terminate before the end of the elongated member 402 or the terminal end of the IV infusion line assembly 400 may be obscured or covered by medical equipment or the patient. In such embodiment, a light may be provided to the optical member 404 in a transverse direction through one or more diffraction optical elements such as an in-coupling grating 438 shown in FIG. 10B. The in-coupling grating 438 includes a plurality of wedges or other lenses that refract light at an angle and allow the light to propagate within the optical member 404 in a longitudinal direction.

Figure 11:
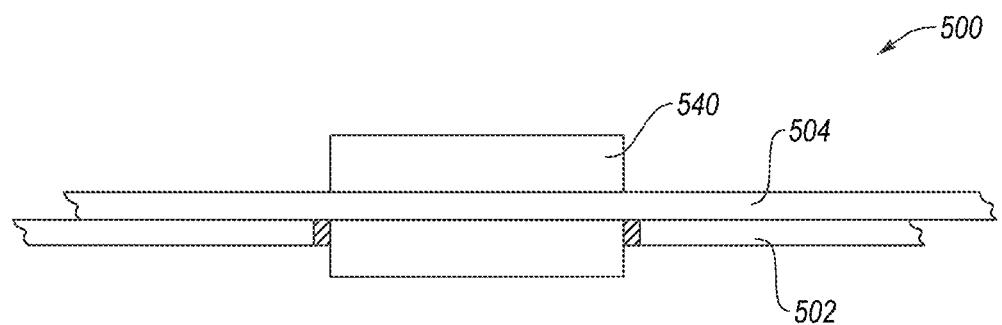
FIG. 11 is a side view of an embodiment of an IV infusion line with an inline filter, according to the present disclosure.

As described herein, the optical member and the elongated member may selectively separable to allow a user to detach at least a portion of the optical member from the elongated member. FIG. 11 illustrates an embodiment of an IV infusion line assembly 500 in which the optical member 504 has been detached from the elongated member 502 and the elongated member 502 is directed through a filter 540. The filter 540 is configured to filter the contents (i.e., therapeutic fluid) of the elongated member 502 while the optical member 504 continues around the filter 540 and rejoins the elongated member 502 on the opposing side of the filter 540.

Figure 12:
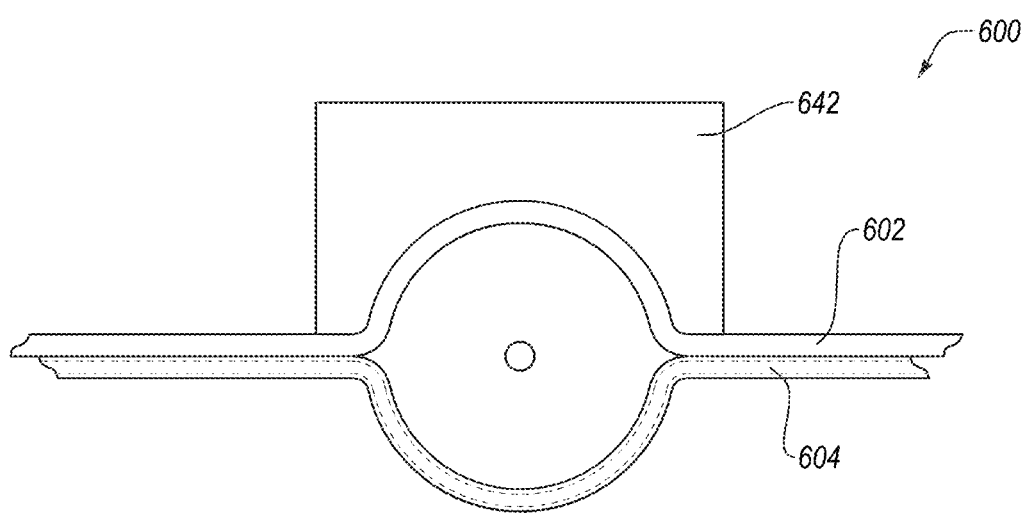
FIG. 12 is a side view of an embodiment of an IV infusion line with an inline rotary pump, according to the present disclosure.

FIG. 12 illustrates an embodiment of an IV infusion line assembly 600 in which the optical member 604 has been detached from the elongated member 602 and the elongated member 602 is directed through a rotary pump 642. The rotary pump 642 is configured to apply a force to the elongated member 602 to urge the contents (i.e., therapeutic fluid) of the elongated member 502 in the longitudinal direction. The optical member 604 continues around the rotary pump 642 and rejoins the elongated member 602 on the opposing side of the rotary pump 642.

At least some of the embodiments of an IV infusion line described herein allow a user to illuminate the IV infusion line using a light source to identify a length of the IV infusion line in a clinical environment. The IV infusion line may be disposable, elongated member and optical member included, and used with conventional adapters and equipment.

Figure 13:
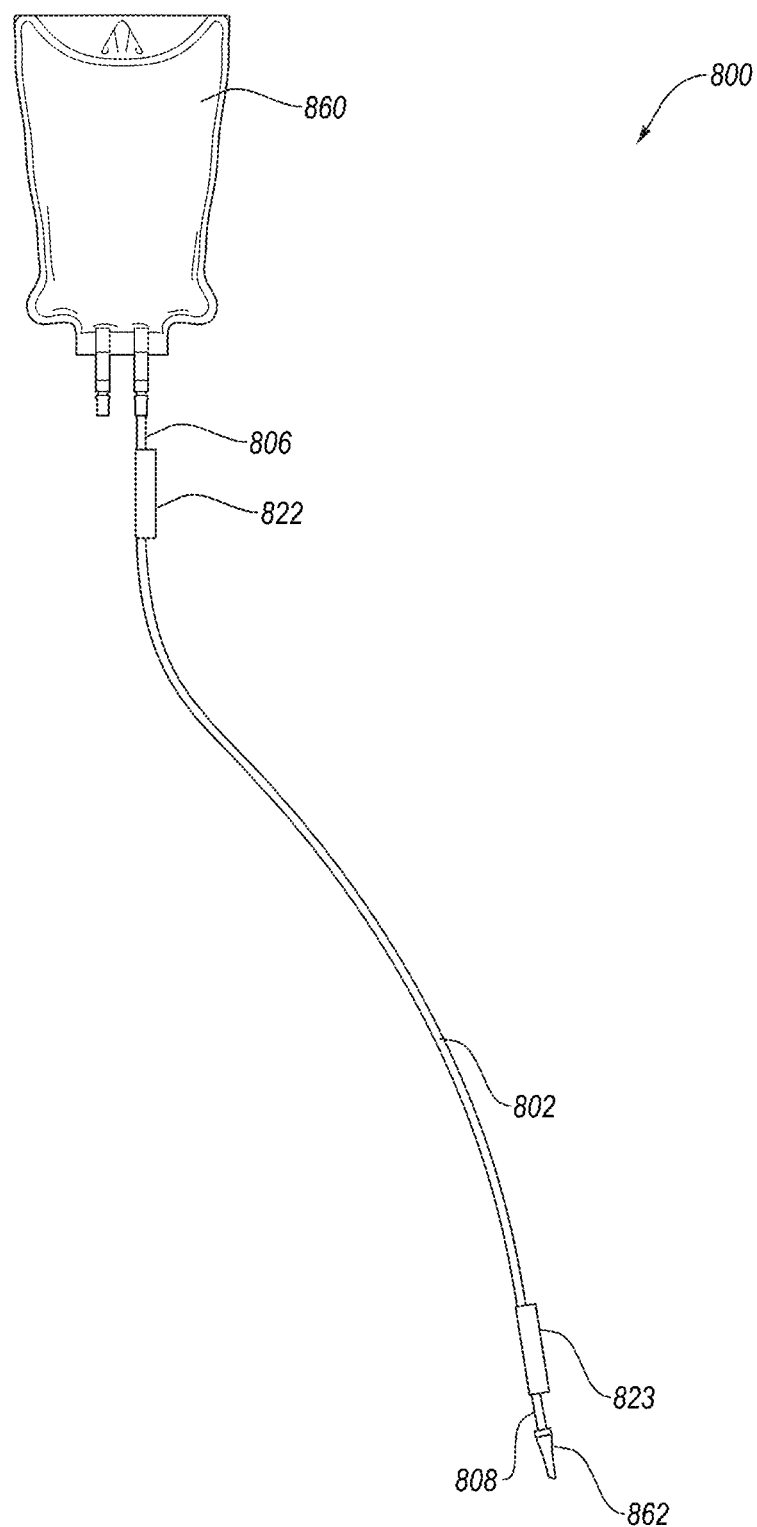
FIG. 13 illustrates another embodiment of an infusion line identification system where a first light component is a light source and where a second light component is also a light source, the light sources being operatively coupled to one another such that both the first and second light components provide synchronous visual identifiers.

FIG. 13 illustrates an alternative embodiment of an infusion line assembly 800. As with other embodiments described herein, the infusion line assembly 800 includes an elongated member 802 and a first light source 822 disposed at a first end 806 of the elongated member 802 (e.g., near an IV bag 860 and associated fluid input). In this embodiment, the optical member is omitted, and instead, the infusion line assembly 800 includes a second light source 823 disposed at a second end 808 of the elongated member 802 (e.g., near a fluid output and patient port 862). The second light source 823 is communicatively coupled to the first light source 822. Thus, rather than using an optical member to transmit light generated by the first light source 822 at the first end 806 to the second end 808, the illustrated embodiment utilizes the two operatively and communicatively coupled light sources 822 and 823 to ensure that the light signal generated at one end of the elongated member 802 has a corresponding light signal generated at the opposite end of the elongated member 802.

The first and second light sources 822 and 823 may be operatively and communicatively coupled via a wireless connection/link. For example, the first and second light sources 822 and 823 may be paired using a Bluetooth wireless link, Wi-Fi, or other suitable wireless communication protocol.

In use, a first light component (in the form of the first light source 822) is positioned near the first end 806 of the elongated member 802 and a second light component (in the form of the second light source 823) is positioned near the second end 808 of the elongated member 802. The first and second light components are operatively coupled to one another (e.g., via a wireless communication link) so that when either is activated, the other is likewise activated. In this manner, a user can activate the first light source 822 or the second light source 823, and the other light source will also automatically be activated, providing a visual indication confirming that each of ends 806 and 808 belong to the same elongated member 802. As stated above, this visual indication can prevent infusion line misidentification and associated accidents and patient risks. For example, a caretaker can quickly and easily use the system to identify which infusion line and/or medicine is attached to which patient vein, and can thereby identify the correct setup quickly and safely.

Figure 14:
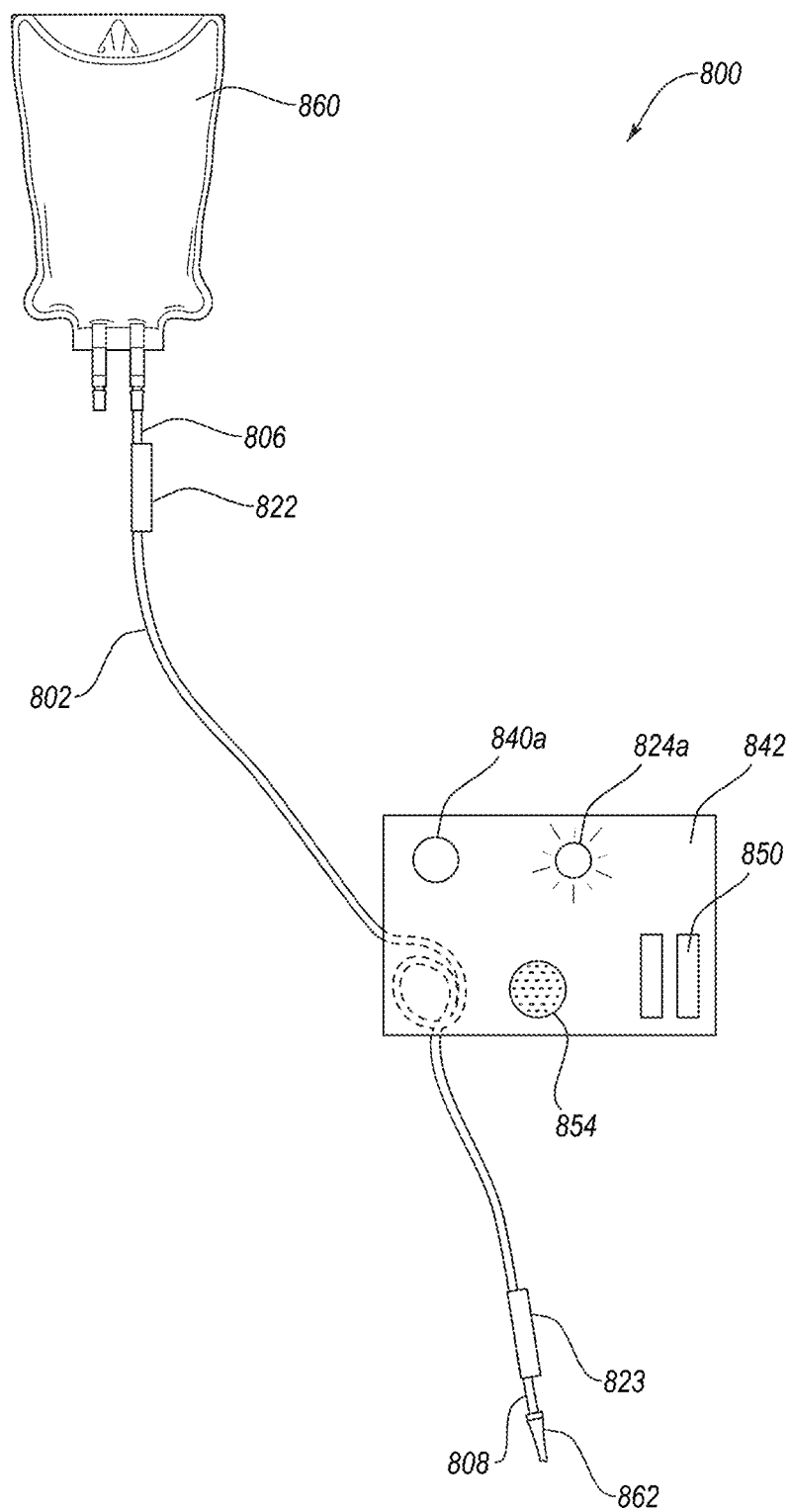
FIG. 14 illustrates an embodiment of an infusion line system as in FIG. 13 with the addition of a pump assembly.

As shown in FIG. 14, the infusion line system can also optionally include a pump assembly 842 attachable or operatively coupled to the elongated member 802. The pump assembly 842 may be provided as a peristaltic pump or other suitable means of moving fluid through the elongated member 802. The pump assembly 842 may also be communicatively coupled (via the aforementioned wireless link) to the first light source 822 and the second light source 823 such that activation of any one of the first light source 822, second light source 823, or pump assembly 842 causes activation of the other components. For example, the pump assembly may be activated when a user actuates a controller 840*a* (the term "controller" also being synonymously referred to herein as a "manual switch"). The controller 840*a* may be provided as a pushbutton, toggle, switch, slider, knob, or other suitable means for selectively activating the device.

Upon activation, the pump assembly 842 may display a visual indicator indicating that the device has been activated. For example, a light 824*a* can turn on to indicate activation of the device. In some embodiments, the light 824*a* is separate from the controller 840*a*. In other embodiments, the light 824*a* may be included in the controller 840*a* itself. For example, the controller 840*a* may be a pushbutton that lights up when activated and turns off when pressed again.

Figure 15:
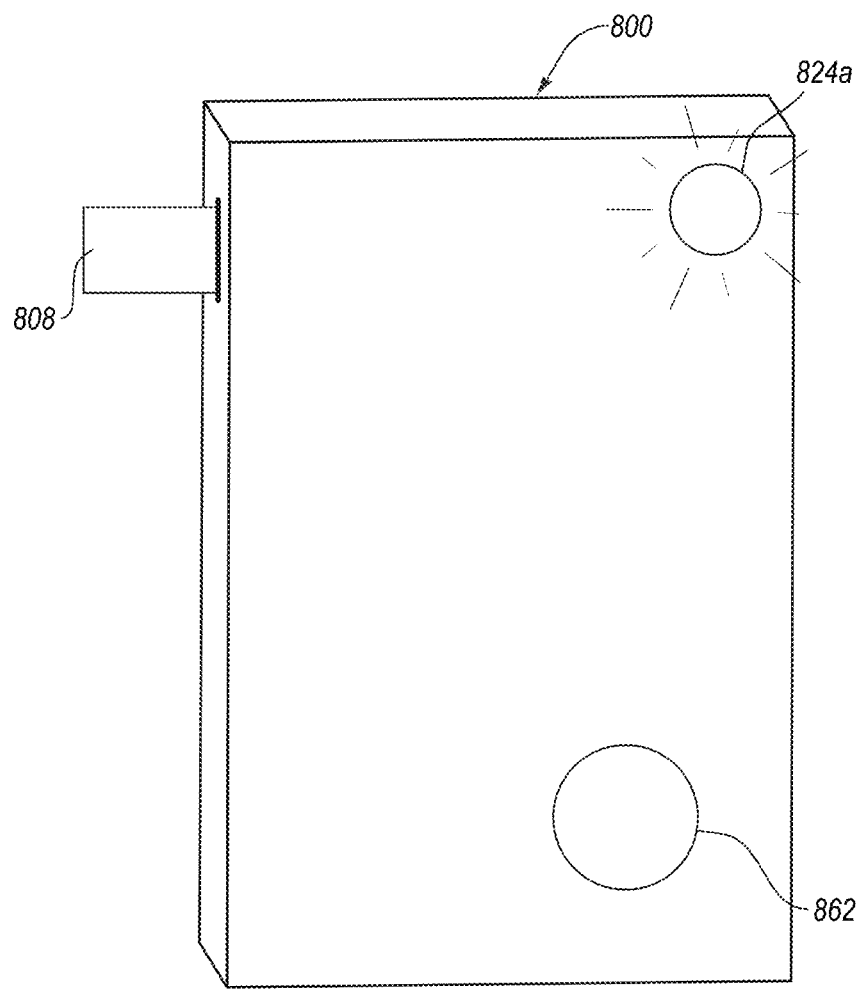
FIG. 15 is a detailed view of a light source of the system of FIG. 13.

Upon activation of the pump assembly 842, corresponding visual indicators (e.g., light 824*b* as shown in FIG. 15) at the first and second light sources 822 and 823 are also automatically activated. The infusion line system 800 need not necessarily be activated by actuating the controller 840*a* of the pump assembly 842. For example, a user may activate any one of the first light source 822, second light source 823, or pump assembly 842 to trigger activation of the corresponding indicators (e.g., light signals) in the other components. In this manner, a user may activate whichever component is closest or is otherwise most convenient to activate, and by so doing can automatically activate all other communicatively linked components of the system.

As shown, the pump assembly 842 may also include one or more stations 850 configured to receive light sources 822 and/or 823. The stations 850 may be configured as charging ports for charging the internal battery/batteries of the light sources 822 and/or 823 when they are plugged in or otherwise attached. The pump assembly 842 may itself be powered by wired connection to a wall outlet and/or may include its own internal battery.

In some embodiments, the pump assembly 842 includes a speaker 854 capable of providing an audible alarm. For example, when a low battery condition is detected in any of the linked light sources, the speaker 854 can be triggered to provide an audible alarm notifying nearby users of the need to replace or otherwise attend to the components. The alarm may additionally or alternatively include other indicators, such as flashing lights at one or more of the pump assembly 842 or the light sources 822, 823, the sending of an error message to other associated devices, etcetera. Either or both of the light sources 822, 823 may include a speaker, either in addition to or as an alternative to the speaker 854 of the pump assembly 842. However, a typical embodiment will omit speakers at the light sources 822, 823.

In some embodiments, two or more components of the infusion line system 800 are provided together as a kit. For example, the two light sources 822 and 823 may be packaged together as a pair. Preferably, the wireless pairing/linking of the two associated light sources will be established prior to packaging, so that the components are ready to use immediately after opening. Pairing/linking prior to packaging can also reduce the risk of error during use, since it will not be necessary for the user to manually pair one or more pairs of lights during installation on corresponding infusion lines. In some embodiments, a kit includes a pair of light sources and the pump assembly 842. Again, it is preferable that these components be wirelessly paired/linked prior to packaging so that the components are more readily used and risks associated with incorrect installation or pairing are reduced. Any of such kits are also preferably sterilized using a suitable sterilization process known in the art, such as a cold sterilization process typically used to sterilize pumps and infusion lines.

FIG. 15 illustrates a detailed view of one of the light sources 822. Since each light source 822 and 823 will typically be similar in size, shape, and construction, only the first light source 822 is shown. However, it will be understood that the second light source 823 may include the same components and features as illustrated. The light source 822 may include any of the other light source embodiments described herein. For example, the light source 822 may include any of the clip features shown in FIGS. 7A and 7B to enable effective attachment to the elongated member 802. In a typical embodiment, the light source 822 will include one or more internal batteries, though other power sources, such as a direct electrical connection to a wall outlet, may additionally or alternatively be utilized.

As with the optional pump assembly 824, the light source 822 includes a visual indicator in the form of a light 824*b* and a corresponding controller 840*b* (also synonymously referred to herein as a "manual switch"). When the controller 840*b* is actuated, the light 824*b* is activated, and the corresponding visual indicators of the other communicatively linked light sources (and pump assembly 842 where applicable) are also automatically activated. As described in reference to the pump assembly 842, the light 842*b* and controller 840*b* may be separate features, as shown, or may alternatively be combined into one manually activatable component such as a pushbutton that lights up upon actuation.

Presently preferred embodiments also include a battery protector 852 configured to prevent accidental activation of the device and/or draining of the battery prior to intended use. The battery protector 852 may be a thin paper, film, or other such structure that partially extends into the light source 822 to break the internal electrical circuit and prevent activation during shipping and storage of the device. For example, the battery protector 852 typically extends across a surface of a battery between the battery and the terminal connector.

A portion of the battery protector 852 (the portion visible in FIG. 15) extends beyond the housing of the light source 822 so that a user can grip the battery protector 852 and pull it away from the light source 822. This allows the internal circuit of the light source 822 to close and allows initiation of the device. Upon initiation, the wireless communication component (e.g., Bluetooth component) of the device will cause the device to search for and seek to establish a communicative link to its associated components (the other light source and optional pump assembly). Once all components have been initiated, the communicative link will be established and the components will be ready for use. The battery/batteries may be designed so that light source operation lasts the duration of a standard IV bag, which is usually about 96 hours.

Certain embodiments may be configured so that the visual indicators activate automatically upon initiation. Additionally, or alternatively, activation and deactivation may be selectively controlled through actuation of the controllers 840*a*, 840*b*, as described by the foregoing.

In some embodiments, the visual indicators of each set of communicatively linked components have corresponding features to distinguish from other sets of communicatively linked components. For example, one pair of linked light sources may have a first color of light when activated while another pair of linked light sources may have a second, different color of light when activated.

Although the foregoing embodiment has been described with reference to two light sources, it will be understood that other light sources may additionally be included as well. For example, some embodiments may include a series of communicatively linked light sources spanning the length of the elongated member 802, such as one or more light sources positioned at intermediate positions between the ends of the elongated member 802.

The articles "a," "an," and "the" are intended to mean that there are one or more of the elements in the preceding descriptions. The terms "comprising," "including," and "having" are intended to be inclusive and mean that there may be additional elements other than the listed elements. Additionally, it should be understood that references to "one embodiment" or "an embodiment" of the present disclosure are not intended to be interpreted as excluding the existence of additional embodiments that also incorporate the recited features. Numbers, percentages, ratios, or other values stated herein are intended to include that value, and also other values that are "about" or "approximately" the stated value, as would be appreciated by one of ordinary skill in the art encompassed by embodiments of the present disclosure. A stated value should therefore be interpreted broadly enough to encompass values that are at least close enough to the stated value to perform a desired function or achieve a desired result. The stated values include at least the variation to be expected in a suitable manufacturing or production process, and may include values that are within 5%, within 1%, within 0.1%, or within 0.01% of a stated value.

A person having ordinary skill in the art should realize in view of the present disclosure that equivalent constructions do not depart from the spirit and scope of the present disclosure, and that various changes, substitutions, and alterations may be made to embodiments disclosed herein without departing from the spirit and scope of the present disclosure. Equivalent constructions, including functional "means-plus-function" clauses are intended to cover the structures described herein as performing the recited function, including both structural equivalents that operate in the same manner, and equivalent structures that provide the same function. It is the express intention of the applicant not to invoke means-plus-function or other functional claiming for any claim except for those in which the words 'means for' appear together with an associated function. Each addition, deletion, and modification to the embodiments that falls within the meaning and scope of the claims is to be embraced by the claims.

The terms "approximately," "about," and "substantially" as used herein represent an amount close to the stated amount that still performs a desired function or achieves a desired result. For example, the terms "approximately," "about," and "substantially" may refer to an amount that is within 95% of, within 99% of, within 99.9% of, or within 99.99% of a stated amount. Further, it should be understood that any directions or reference frames in the preceding description are merely relative directions or movements. For example, any references to "up" and "down" or "above" or "below" are merely descriptive of the relative position or movement of the related elements.

Elements described in relation to any embodiment depicted and/or described herein may be substituted for or combined with elements described in relation to any other embodiment depicted and/or described herein. For example, any of the components or features described in relation to the light source 722 of FIG. 7 may be substituted for or combined with any of the components or features described in relation to the IV infusion line assembly 200, and vice versa.

The present invention may be embodied in other specific forms without departing from its spirit or characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A kit for providing visual identification of an infusion line, the kit comprising:
   a first light source configured for selective attachment to an infusion line, the first light source being actuatable to generate a light signal upon actuation;
   a second light source configured for selective attachment to an infusion line, the second light source being actuatable to generate a light signal upon actuation,
   wherein the first and second light sources are communicatively connectable to one another via a wireless connection,
   wherein the first light source is configured to, upon actuation,
      (i) generate a light signal at the first light source,
      (ii) automatically establish the wireless connection with second light source, and
      (iii) automatically activate the second light source to cause the second light source to generate a light signal at the second light source, and
   wherein the second light source is configured to, upon actuation,
      (i) generate a light signal at the second light source,
      (ii) automatically establish the wireless connection with the first light source, and
      (iii) automatically activate the first light source to cause the first light source to generate a light signal at the first light source.

2. The kit of claim 1, wherein the first light source, the second light source, or both include a manual switch to enable actuation.

3. The kit of claim 1, wherein the first light source, the second light source, or both include one or more clips enabling the selective attachment to an infusion line.

4. The kit of claim 1, wherein the first light source, the second light source, or both include a battery protector configured to prevent actuation until the battery protector has been removed.

5. The kit of claim 1, wherein the first light source, the second light source, or both are configured to provide light for a duration of about 72 to 120 hours.

6. The kit of claim 1, further comprising an additional light source, wherein the additional light source is communicatively connectable to the first and second light sources via the wireless connection, and wherein the additional light source is configured to automatically generate a light signal upon actuation of the first light source and/or second light source.

7. The kit of claim 6, wherein the additional light source is a pump assembly that includes a light.

8. The kit of claim 7, wherein the pump assembly includes a peristaltic pump.

9. The kit of claim 7, wherein the pump assembly includes one or more charging ports for receiving the first and/or second light source to charge the first and/or second light source.

10. The kit of claim 1, wherein the wireless connection is an ultrahigh frequency radio wave connection.

11. An infusion line assembly, comprising:
    an infusion line configured for administering fluid to a patient;
    a first light source configured for selective attachment to the infusion line, the first light source being actuatable to generate a light signal upon actuation;
    a second light source configured for selective attachment to the infusion line, the second light source being actuatable to generate a light signal upon actuation,
    wherein the first and second light sources are communicatively connectable to one another via a wireless connection,
    wherein the first light source is configured to, upon actuation,
       (i) generate a light signal at the first light source,
       (ii) automatically establish the wireless connection with second light source, and
       (iii) automatically activate the second light source to cause the second light source to generate a light signal at the second light source, and
    wherein the second light source is configured to, upon actuation,
       (i) generate a light signal at the second light source,
       (ii) automatically establish the wireless connection with the first light source, and
       (iii) automatically activate the first light source to cause the first light source to generate a light signal at the first light source.

12. The assembly of claim 11, wherein the first light source, the second light source, or both include a manual switch to enable actuation.

13. The assembly of claim 11, wherein the first light source, the second light source, or both include one or more clips enabling the selective attachment to an infusion line.

14. The assembly of claim 11, further comprising an additional light source, wherein the additional light source is communicatively connectable to the first and second light sources via the wireless connection, and wherein the additional light source is configured to automatically generate a light signal upon actuation of the first light source and/or second light source.

15. The assembly of claim 14, wherein the additional light source is a pump assembly that includes a light.

16. A method of modifying an infusion line to enhance identifiability of the infusion line, the method comprising:

attaching a first light source to the infusion line, the first light source being actuatable to generate a light signal upon actuation;

attaching a second light source to the infusion line, the second light source being actuatable to generate a light signal upon actuation, wherein the first and second light sources are communicatively connectable to one another via a wireless connection, wherein the first light source is configured to, upon actuation,
(i) generate a light signal at the first light source,
(ii) automatically establish the wireless connection with second light source, and
(iii) automatically activate the second light source to cause the second light source to generate a light signal at the second light source, and wherein the second light source is configured to, upon actuation,
(i) generate a light signal at the second light source,
(ii) automatically establish the wireless connection with the first light source, and
(iii) automatically activate the first light source to cause the first light source to generate a light signal at the first light source; and actuating one of the first or second light sources to cause generation of light signals at both the first and second light sources.

17. The method of claim 16, wherein the first light source, the second light source, or both include a manual switch to enable actuation.

18. The method of claim 16, wherein actuating one of the first or second light sources to cause generation of light signals at both the first and second light sources also causes generation of a light signal at an additional light source that is communicatively connectable to the first and second light sources via the wireless connection.

19. The method of claim 18, wherein the additional light source is a pump assembly that includes a light.

* * * * *